US006066671A

United States Patent [19]
Yanni et al.

[11] Patent Number: 6,066,671
[45] Date of Patent: May 23, 2000

[54] TREATMENT OF GLC1A GLAUCOMA WITH 3-BENZOYL-PHENYLACETIC ACIDS, ESTERS, OR AMIDES

[75] Inventors: John M. Yanni, Burleson; Mark R. Hellberg, Arlington, both of Tex.

[73] Assignee: Alcon Laboratories, Inc., Fort Worth, Tex.

[21] Appl. No.: 08/994,903

[22] Filed: Dec. 19, 1997

[51] Int. Cl.[7] .................................................. A61K 31/165
[52] U.S. Cl. ........................ 514/619; 514/535; 514/570; 514/617; 514/618; 514/621; 514/913
[58] Field of Search .................... 514/535, 570, 514/617, 618, 619, 621, 913

[56] References Cited

U.S. PATENT DOCUMENTS

| | | | |
|---|---|---|---|
| 5,475,034 | 12/1995 | Yanni et al. | 514/619 |
| 5,606,043 | 2/1997 | Nguyen et al. | 536/23.5 |

FOREIGN PATENT DOCUMENTS

| | | | |
|---|---|---|---|
| 0 221 753 | 5/1987 | European Pat. Off. | C07C 87/50 |
| 2 059 963 | 4/1981 | United Kingdom | C07C 103/00 |
| WO 95/17178 | 5/1995 | WIPO | |
| WO 96/40102 | 12/1996 | WIPO | A61K 31/19 |
| WO 96/40103 | 12/1996 | WIPO | A61K 31/19 |

OTHER PUBLICATIONS

"Mapping of a Gene for Autosomal Dominant Juvenile–Onset Open–Angle Glaucoma to Chromosome Iq", Richards, et al., American Journal of Human Genetics, vol. 54, Jan. 1, 1994, pp. 62–70.

"Fine Mapping of the Autosomal Dominant Juvenile Open Angle Glaucoma (CLC1A) Region and Evaluation of Candidate Genes", Sunden et al., Genome Research, vol. 6, No. 9, Sep. 1996, pp. 862–869.

"Cellular Pharmacology and Molecular Biology of the Trabecular Meshwork Inducible Glucocorticoid Response Gene Product", Polansky et al., Ophthalmologica, vol. 211, No. 3, May 1997, pp. 126–139.

"In Vitro Correlates of Glucocorticoid Effects on Intraocular Pressure", Polansky et al, Glaucoma Update, Jan. 1991, pp. 20–29.

Sommer A, et al. Relationship between intraocular pressure and primary open angle glaucoma among white and black Americans. Arch. Ophthalmol. 109:1090–1095, (1991).

Sheffield, et al., "Genetic Linkage of Familial Open Angle Glaucoma to Chromosome 1q21–q31," Nature Genetics, 4:47–50 (1993).

Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995).

Akarsu, et al., "A Second Locus (GLC3B) for Primary Congenital Glaucoma (Buphthalmos) Maps to the 1p36 Region," Human Molecular Genetics, 5(8): 1199–1203 (1996).

Stoilova, et al., "Localization of a Locus (GLC1B) for Adult–Onset Primary Open Angle Glaucoma to the 2cen–q13 Region," Genomics, 36:142–150 (1996).

Wirtz, et al., "Mapping a Gene for Adult–Onset Primary Open–Angle Glaucoma to Chromosome 3q," Am. J. Hum. Genet., 60:296–304 (1997).

Andersen, et al., "A Gene Responsible for the Pigment Dispersion Syndrome Maps to Chromosome 7q35–q36," Arch. Ophthalmol., 115:384–388 (1997).

Richards, et al., "Mapping of a Gene for Autosomal Dominant Juvenile–Onset Open–Angle Glaucoma to Chromosome 1q," Am. J. Hum. Genet., 54:62–70 (1994).

Morissette, et al., "A Common Gene for Juvenile and Adult–Onset Primary Open–Angle Glaucomas Confined on Chromosome 1q," Am. J. Hum. Genet., 56:1431–1442 (1995).

Wiggs, et al., "Genetic Linkage of Autosomal Dominant Juvenile Glaucoma to 1q21–q31 in Three Affected Pedigrees," Genomics, 21:299–303 (1994).

Meyer, et al., "Age–Dependent Penetrance and Mapping of the Locus for Juvenile and Early–Onset Open–Angle Glaucoma on Chromosome 1q (GLC1A) in a French Family," Hum. Genet., 98:567–571 (1996).

Graff, et al., "Confirmation of Linkage to 1q21–31 in a Danish Autosomal Dominant Juvenile–Onset Glaucoma Family and Evidence of Genetic Heterogeneity," Hum. Genet., 96:285–289 (1995).

Stone, et al., "Identification of a Gene That Causes Primary Open Angle Glaucoma," Science, 275:668–670 (1997).

Polansky, et al., "In Vitro Correlates of Glucocorticoid Effects on Intraocular Pressure," Glaucoma Update IV (1991).

Polansky, et al., "Cellular Pharmacology and Molecular Biology of the Trabecular Meshwork Inducible Glucocorticoid Response Gene Product," Ophthalmologica, 211:126–139 (1997).

Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," FEBS Letters, 413:349–353 (1997).

(Kubota, et al., "A Novel Myosin–like Protein (Myocilin) Expressed in the Connecting Cilium of the Photoreceptor: Molecular Cloning, Tissue Expression, and Chromosomal Mapping," Genomics, 41:360–369 (1997).

(List continued on next page.)

*Primary Examiner*—Zohreh Fay
*Attorney, Agent, or Firm*—Sally Yeager

[57] ABSTRACT

Compositions of 3-benzoylphenylacetic acid derivatives for treating GLC1A glaucoma and methods for their use are disclosed.

2 Claims, 2 Drawing Sheets

OTHER PUBLICATIONS

Sunden, et al., "Fine Mapping of the Autosomal Dominant Juvenile Open Angle Glaucoma (GLC1A) Region and Evaluation of Candidate Genes," Genome Research, 6:862–869 (1996).

Adam, et al., "Recurrent Mutations in a Single Exon Encoding the Evolutionarily Conserved Olfactomedin–Homology Domain of TIGR in Familial Open–Angle Glaucoma," Human Molecular Genetics, 6(12):2091–2097 (1997).

Rozsival, et al., "Aqueous Humour and Plasma Cortisol Levels in Glaucoma and Cataract Patients," Current Eye Research, 1:391–396 (1981).

Schwartz, et al., "Increased Plasma Free Cortisol in Ocular Hypertension and Open Angle Glaucoma," Arch. Ophthalmol., 105:1060–1065 (1987).

Wilson, et al., Dexamethasone Induced Ultrastructural Changes in Cultured Human Trabecular Meshwork Cells, Cur. Eye Res., 12:783–793 (1993).

Clark, et al., "Glucocorticoid–Induced Formation of Cross–Linked Actin Networks in Cultured Human Trabecular Meshwork Cells," Invest. Ophthalmol. Vis. Sci., 35:281–294 (1994).

Maximum Potential Drug Concentration
in Various Ocular Compartments

| Compartment | Concentration ($\mu M$) |
| --- | --- |
| Cornea | 200 |
| Iris-Ciliary Body | 29 |
| Aqueous Humor | 24 |
| Choroid | 0.4 |
| Retina | 0.2 |

FIG. 2 ature of the disease. Despite these problems, a number of families with heritable forms of glaucoma have been identified and these families have been used to map a variety of glaucoma genes (Sheffield, et al., "Genetic Linkage of Familial Open Angle Glaucoma to Chromosome 1q21–q31, "Nature Genetics, 4:47–50 (1993); Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995); Akarsu, et al., "A Second Locus (GLC3B) for Primary Congenital Glaucoma (Buphthalmos) Maps to the 1p36 Region," Human Molecular Genetics, 5(8):1199–1203 (1996); Stoilova, et al., "Localization of a Locus (GLC1B) for Adult-Onset Primary Open Angle Glaucoma to the 2cen-q13 Region," Genomics, 36:142–150 (1996); Wirtz, et al., "Mapping a Gene for Adult-Onset Primary Open-Angle Glaucoma to Chromosome 3q," Am. J. Hum. Genet., 60:296–304 (1997); Andersen, et al., "A Gene Responsible for the Pigment Dispersion Syndrome Maps to Chromosome 7q35–q36," Arch. Ophthalmol., 115:384–388 (1997). The first glaucoma gene mapped (GLC1A) was in a large family with autosomal dominant inherited juvenile glaucoma (JG). This disease is characterized by an early disease onset (at the age of late teens to early 20s), relatively high IOPs, and general resistance to conventional pharmacological IOP lowering therapy. The GLC1A gene was mapped by positional cloning and linkage analysis to chromosome 1q22–25 (Sheffield et al, Id., and a number of other groups have confirmed the 1q location of this juvenile glaucoma gene (Richards, et al., "Mapping of a Gene for Autosomal Dominant Juvenile-Onset Open-Angle Glaucoma to Chromosome 1q," Am. J. Hum. Genet., 54:62–70 (1994); Morissette, et al., "A Common Gene for Juvenile and Adult-Onset Primary Open-Angle Glaucomas Confined on Chromosome 1q," Am. J. Hum. Genet., 56:1431–1442 (1995); Wiggs, et al., "Genetic Linkage of Autosomal Dominant Juvenile Glaucoma to 1q21–q31 in Three Affected Pedigrees," Genomics, 21:299–303 (1994); Meyer, et al., "Age-Dependent Penetrance and Mapping of the Locus for Juvenile and Early-Onset Open-Angle Glaucoma on Chromosome 1q (GLC1A) in a French Family," Hum. Genet., 98:567–571 (1996); Graff, et al., "Confirmation of Linkage to 1q21–31 in a Danish Autosomal Dominant Juvenile-Onset Glaucoma Family and Evidence of Genetic Heterogeneity," Hum. Genet., 96:285–289 (1995). Glaucoma due to the GLC1A gene is often referred to as 1q glaucoma.

The GLC1A gene was identified as encoding a 57 kD protein expressed in the trabecular meshwork (TM) (Stone, et al., "Identification of a Gene That Causes Primary Open Angle Glaucoma," Science, 275:668–670 (1997). The expression of the GLC1A gene, and the encoded TM protein, is up-regulated by glucocorticoids (Polansky, et al., "In Vitro Correlates of Glucocorticoid Effects on Intraocular Pressure," Glaucoma Update IV (1991); and Polansky, et al., "Cellular Pharmacology and Molecular Biology of the Trabecular Meshwork Inducible Glucocorticoid Response Gene Product," Ophthalmologica, 211:126–139 (1997) This TM protein is also known as TIGR (trabecular meshwork inducible glucocorticoid response) (Polansky, Id.). The glucocorticoid-induction of this TM protein has been suggested to be involved in the generation of glucocorticoid-induced ocular hypertension and glaucoma (Polansky, Id.).

The GLC1A gene is expressed in other ocular tissues such as the ciliary epithelium (Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," FEBS Letters, 413:349–353 (1997) and the retina (Kubota, et al., "A Novel Myosin-like Protein (Myocilin) Expressed in the Connecting Cilium of the Photoreceptor: Molecular Cloning, Tissue Expression, and Chromosomal Mapping,"Genomics, 41:360–369 (1997). The gene is referred to by several names including GLC1A (Sheffield, supra; Sunden, et al., "Fine Mapping of the Autosomal Dominant Juvenile Open Angle Glaucoma (GLC1A) Region and Evaluation of Candidate Genes," Genome Research, 6:862–869 (1996); Stone, et al., supra, TIGR (Polansky supra; Ortego, supra, and myocilin (Kubota, supra). Mutations GLC1A are not only responsible for juvenile glaucoma, but also a significant subset of adult onset primary open angle glaucoma (Stone, et al., supra; Adam, et al., "Recurrent Mutations in a Single Exon Encoding the Evolutionarily Conserved Olfactomedin-Homology Domain of TIGR in Familial Open-Angle Glaucoma," Human Molecular Genetics, 6(12):2091–2097 (1997). The 1q glaucoma gene (GLC1A, TIGR) is the subject of Nguyen, et al., U.S. Pat. No. 5,606,043, issued Feb. 25, 1997.

Several patent applications have disclosed the use of non-steroidal cyclooxygenase inhibitors to treat intraocular pressure (WO 95/17178) through the action of the compounds on trabecular meshwork cells (WO 96/40103 and WO 96/40102). At least some of the beneficial effects of the non- steroidal cyclooxygenase inhibitors are attributed to the inhibition of the expression of myocilin (or TIGR) which is the gene product of GLC1A.

It is known that trabecular meshwork cells have glucocorticoid receptors and that glucocorticoid binding with these receptors causes a change in trabecular meshwork cell gene expression. Known manifestations of this change include a reorganization of the cytoskeleton (Wilson, et al., "Dexamethasone Induced Ultrastructural Changes in Cultured Human Trabecular Meshwork Cells, Cur. Eye Res., 12:783–793 (1993), and Clark, et al., "Glucocorticoid-Induced Formation of Cross-Linked Actin Networks in Cultured Human Trabecular Meshwork Cells," Invest. Ophthalmol. Vis. Sci., 35:281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure is maintained or frequently occurs, the optic nerve head can be damaged resulting in the loss of visual field. Loss of visual field is the hallmark symptom associated with glaucoma.

In summary, the GLC1A gene product can lead to the development of ocular hypertension and glaucoma in one of two ways: (1) mutations in GLC1A are responsible for most forms of juvenile glaucoma and a subset of adult onset POAG or (2) exposure of some individuals to glucocorticoids leads to increased GLC1A expression in the TM which causes increased aqueous humor outflow resistance and the development of ocular hypertension. The precise mechanism(s) responsible for GLC1A effects on IOP are currently unknown.

SUMMARY OF THE INVENTION

Certain non-steroidal cyclooxygenase inhibitors and their pharmaceutical formulations are useful for treating GLC1A glaucoma. The invention is also directed to methods for controlling GLC1A glaucoma using the non-steroidal cyclooxygenase inhibitors.

BRIEF DESCRIPTION OF DRAWINGS

FIG. 2 shows the nepafenac concentration calculated from the data in FIG. 1.

DESCRIPTION OF PREFERRED EMBODIMENTS

Figure 1:
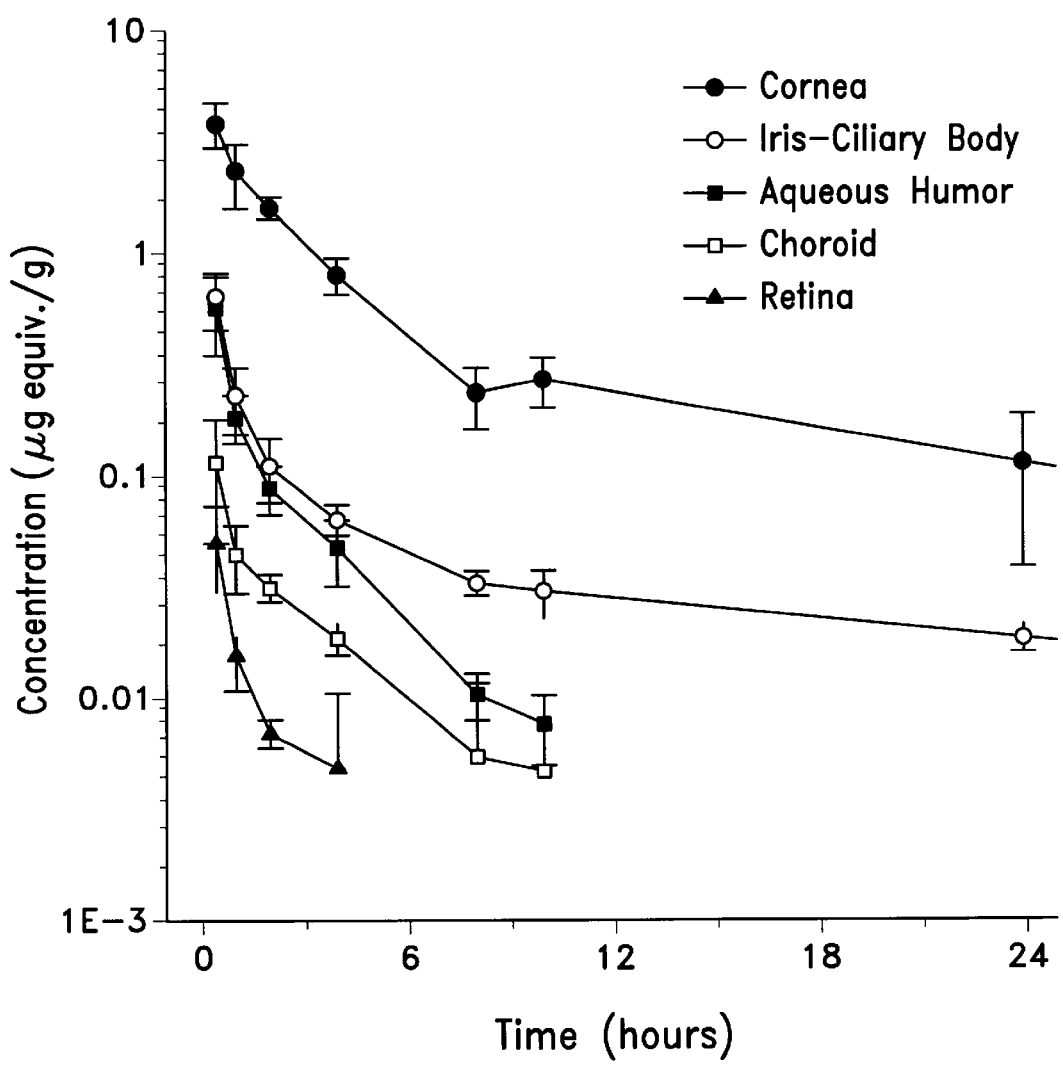
FIG. 1 shows nepafenac concentrations in ocular tissues of rabbits following a single topical dose.

Agents which alter the expression of GLC1A in the glaucomatous eye are expected to lower IOP and thereby prevent or inhibit the glaucomatous optic neuropathy which is being driven by elevated IOP. Glucocorticoids upregulate GLC1A expression in the TM of certain individuals. There have been several reports of elevated levels of the natural glucocorticoid cortisol in the aqueous humor and plasma of glaucoma patients (Schwartz, et al., supra; Rozsival, et al., supra. In addition, certain mutations in GLC1A may alter the expression of GLC1A in the TM tissue of 1q glaucoma patients. Unexpectedly, it has been discovered that certain non-steroidal cyclooxygenase inhibitors inhibit the expression of GLC1A in cultured human TM cells and lower elevated IOP in certain animal models of ocular hypertension. The non-steroidal cyclooxygenase inhibitors act to prevent the expression of GLC1A and the subsequent development of ocular hypertension.

Many non-steroidal cyclooxygenase inhibitors do not readily penetrate the cornea upon topical administration and, therefore, do not reach therapeutic concentrations in the target tissue, the trabecular meshwork.

A series of compounds disclosed in commonly assigned U.S. Pat. No. 5,475,034, which showed no significant non-steroidal anti-inflammatory activity *in vitro*, exhibit superior corneal penetration leading to improved ocular bioavailability. The estimated concentration within the anterior chamber following topical ocular administration of 0.3% nepafenac to rabbits is 24 μM (see FIGS. 1 and 2). This concentration, achieved using a simple formulation without penetration enhancers, is in excess of the parent compounds' COX I and COX II $IC_{50}$s. This enhanced bioavailability provides a significant advantage and is unexpected over other non-steroidal anti-inflammatory drugs as well as amide derivatives of non-steroid anti-inflammatory drugs. The compounds disclosed in the '034 patent, the contents of which are incorporated herein by reference, are ester and amide derivatives of 3-benzoylphenylacetic acid.

The compounds set forth in the '034 patent have the following structure:

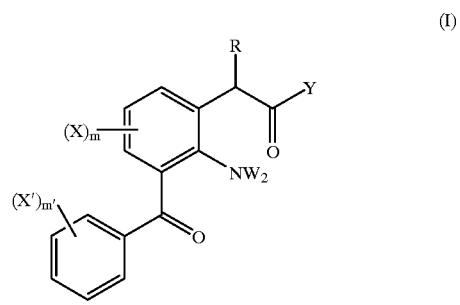

(I)

R=H, $C_{1-4}$ (un)branched alkyl, $CF_3$, $SR^4$

Y=OR', NR" R'

R'=H (except when Y=OR'), $C_{1-10}$ (un)branched alkyl, (un)substituted (substitution as defined by X below), (un)substituted heterocycle (substitution as defined by X below), —$(CH_2)_n Z(CH_2)_{n'} A$ n=2–6 n'=1–6

Z=nothing, O, C=O, OC(=O), C(=O)O, C(=O)$NR^3$, $NR^3$C(=O), S(O)$_{n^2}$, $CHOR^3$, $NR^3$ $n^2$=0–2

$R^3$=H, $C_{1-6}$ (un)branched alky, (un)substituted aryl (substitution as defined by X below), (un)substituted heterocycle (substitution as defined by X below)

A=H, OH, optionally (un)substituted aryl (substitution as defined by X below), (un)substituted heterocycle (substitution as defined by X below), —$(CH_2)_n OR^3$

R"=H, OH, OR'

X and X' independently=H, F, Cl, Br, I, OR', CN, OH, S(O)$_{n^2}R^4$, $CF_3$, $R^4$, $NO_2$ $R^4=C_{1-6}$ (un)branched alkyl m=0–3 m'=0–5

W=O,H

Preferred compounds for use in the pharmaceutical compositions or method of the present invention are those of Formula I wherein:

R=H, $C_{1-2}$ alkyl

Y=NR'R"

R'H, $C_{1-6}$ (un)branched alkyl, —$(CH_2)_n Z (CH_2)_{n'} A$

Z=nothing, O, $CHOR^3$, $NR^3$ $R_3$=H

A=H, OH, (un)substituted aryl (substitution as defined by X below)

X and X' independently=H, F, Cl, Br, CN, $CF_3$, OR', $SR^4$, $R^4$

R"=H
R⁴=C₁₋₄ (un)branched alkyl
m=0–2
m'=0–2
W=H
n=2–4
n'=0–3

The most preferred compounds for use in the compositions or method of the present invention are 2-Amino-3-(4-fluorobenzoyl)-phenylacetamide; 2-Amino-3-benzoyl-phenylacetamide (nepafenac); and 2-Amino-3-(4-chlorobenzoyl)phenylacetamide.

For the preferred compound, nepafenac, W=H, R=H, Y=NH₂, X'=H, X=H, m=3, and m'=5.

The compounds are administered topically to the eye at a concentration of 0.001%–1% (w/v), preferably 0.05–0.5% (w/v) one to three times per day according to the discretion of a skilled clinician.

The following examples are illustrative of formulations which can be used according to the present invention, but are not limiting. "Active Agent" means one or more compounds described by the structure and definition set forth above.

| | |
|---|---|
| Active agent | 0.01–0.5% |
| Polysorbate 80 | 0.01% |
| Benzalkonium Chloride | 0.01% + 10% excess |
| Disodium EDTA | 0.1% |
| Monobasic Sodium Phosphate | 0.03% |
| Dibasic Sodium Phosphate | 0.1% |
| Sodium Chloride | q.s. 290–300 mOsm/Kg |
| pH adjustment with NaOH and/or HCl | pH 4.2–7.4 |
| Water | q.s. 100% |

| | |
|---|---|
| Active agent | 0.01–0.5% |
| Hydroxypropyl Methylcellulose | 0.5% |
| Polysorbate 80 | 0.01% |
| Benzalkonium Chloride | 0.01% + 5% excess |
| Disodium EDTA | 0.01% |
| Dibasic Sodium Phosphate | 0.2% |
| Sodium Chloride | q.s. 290–300 mOsm/Kg |
| pH adjustment with NaOH and/or HCl | pH 4.2–7.4 |
| Water | q.s. 100% |

We claim:

1. A method for treating GLC1A glaucoma which comprises topically administering to the eye a pharmaceutically effective amount of a compound of the structure:

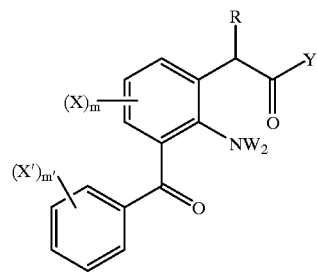

(I)

R=H, $C_{1-4}$ (un)branched alkyl, $CF_3$, $SR^4$

Y=OR', NR"R'

R'=H (except when Y=OR'), $C_{1-10}$ (un)branched alkyl, (un)substituted (substitution as defined by X below), (un)substituted heterocycle (substitution as defined by X below), —$(CH_2)_n Z(CH_2)_{n'} A$ n=2–6 n'=1–6

Z=nothing, O, C=O, OC(=O), C(=O)O, C(=O)NR³, NR³C(=O), S(O)$_n$2, CHOR³, NR³

$n^2$=0–2

R³=H, $C_{1-6}$ (un)branched alkyl, (un)substituted aryl (substitution as defined by X below), (un)substituted heterocycle (substitution as defined by X below)

A=H, OH, optionally (un)substituted aryl (substitution as defined by X below), (un)substituted heterocycle (substitution as defined by X below), —$(CH_2)_n OR^3$

R"=H, OH, OR'

X and X' independently=H, F, Cl, Br, I, OR', CN, OH, S(O)$_n$2R⁴, $CF_3$, $R^4$, $NO_2$ R⁴=$C_{1-6}$ (un)branched alkyl m=0–3 m'=0–5

W=O, H.

2. The method of claim 1 wherein W=H, R=H, Y=NH₂, X'=H, X=H, m=3, and m'=5.

* * * * *